United States Patent
Drewry et al.

(10) Patent No.: US 7,901,434 B2
(45) Date of Patent: Mar. 8, 2011

(54) VERTEBRAL ROD ASSEMBLIES AND METHODS

(75) Inventors: Troy D. Drewry, Memphis, TN (US); William Barry Null, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 111 days.

(21) Appl. No.: 12/362,095

(22) Filed: Jan. 29, 2009

(65) Prior Publication Data

US 2009/0138049 A1    May 28, 2009

Related U.S. Application Data

(62) Division of application No. 11/313,000, filed on Dec. 20, 2005, now Pat. No. 7,517,359.

(51) Int. Cl.
*A61B 17/70* (2006.01)
*F16B 7/10* (2006.01)

(52) U.S. Cl. .................. 606/256; 606/259; 403/83

(58) Field of Classification Search .......... 606/250–253, 606/256, 257, 259, 260, 264, 278; 403/24, 403/25, 91, 96, 97
See application file for complete search history.

(56) References Cited

U.S. PATENT DOCUMENTS

| | | | | |
|---|---|---|---|---|
| 5,486,174 | A * | 1/1996 | Fournet-Fayard et al. | ... 606/261 |
| 6,241,730 | B1 * | 6/2001 | Alby | 606/256 |
| 6,328,741 | B1 * | 12/2001 | Richelsoph | 606/252 |
| 7,175,622 | B2 * | 2/2007 | Farris | 606/250 |
| 7,635,380 | B2 * | 12/2009 | Zucherman et al. | 606/267 |
| 2005/0113927 | A1 * | 5/2005 | Malek | 623/17.16 |
| 2005/0228376 | A1 * | 10/2005 | Boomer et al. | 606/61 |
| 2005/0228378 | A1 * | 10/2005 | Kalfas et al. | 606/61 |
| 2006/0058787 | A1 * | 3/2006 | David | 606/61 |

* cited by examiner

*Primary Examiner* — Eduardo C Robert
*Assistant Examiner* — Ellen C Hammond

(57) ABSTRACT

A vertebral rod assembly with first and second members that may rotate about a first axis. Each of the first and second members includes a base and a vertebral support rod extending from the base. An extension extends from the base on the first member into an opening formed in the base of the second member. A ring is sized to extend around the extension. A fastener engages with the ring to lock the first and second members, and to prevent relative rotation between the first member and second member.

20 Claims, 10 Drawing Sheets

VERTEBRAL ROD ASSEMBLIES AND METHODS

RELATED APPLICATION

The present application is a divisional application of previously-filed U.S. patent application Ser. No. 11/313,000, filed on Dec. 20, 2005, herein incorporated by reference in its entirety.

BACKGROUND

The present application relates generally to spinal implant assemblies, and more particularly to a vertebral rod system having first and second connectable and adjustable members.

The spine is divided into four regions comprising the cervical, thoracic, lumbar, and sacrococcygeal regions. The cervical region includes the top seven vertebrae identified as C1-C7. The thoracic region includes the next twelve vertebrae identified as T1-T12. The lumbar region includes five vertebrae L1-L5. The sacrococcygeal region includes nine fused vertebrae that form the sacrum and the coccyx. The vertebrae of the spine are aligned in a curved configuration that includes a cervical curve, thoracic curve, and lumbosacral curve.

Vertebral rods may be implanted to support and position the vertebrae in one or more of these regions. The rods extend along a section of the spine and are connected to the vertebrae with one or more fasteners. The rods may have a curved configuration to conform to the curvature of the spine. Often times two or more rods are connected together and work in combination to support and position the vertebrae. The rods may have the same or different shapes and sizes depending upon their position along the spine.

SUMMARY

The present application relates to a vertebral rod assembly. The vertebral rod assembly may comprise first and second members that may rotate with respect to each other about a first axis. Each of the first and second members may include a base and a vertebral support rod extending from the base. The base on the first member includes an extension member that extends into an opening formed in the base of the second member. A ring may extend around the extension and may fit within the base of the second member. A fastener may extend through a sidewall of the second member and the ring to lock the first and second members, and to prevent the rotation of the first member and second member.

DETAILED DESCRIPTION

Figure 1:
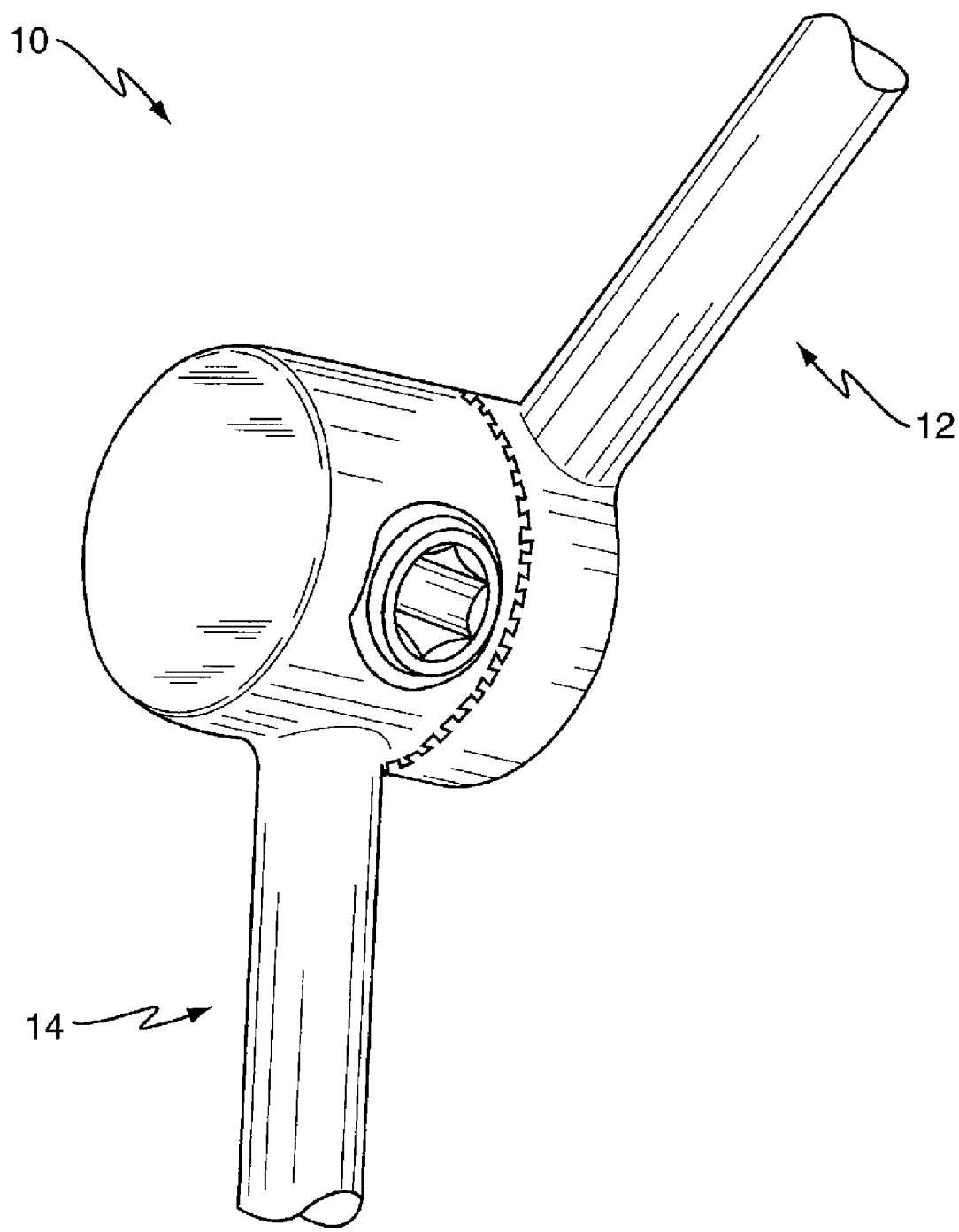
FIG. 1 is a perspective view of a vertebral rod assembly according to one embodiment.

The present application is directed to vertebral rod assemblies, with one embodiment generally illustrated as element 10 in FIG. 1, having first and second members 12, 14. Members 12, 14 are selectively positionable at a variety of angles to conform to the curvature of the patient's spine. Each member 12, 14 includes a rod and a base. A locking device locks the position of the members 12, 14 at the desired orientation to prevent further movement.

Figure 2:
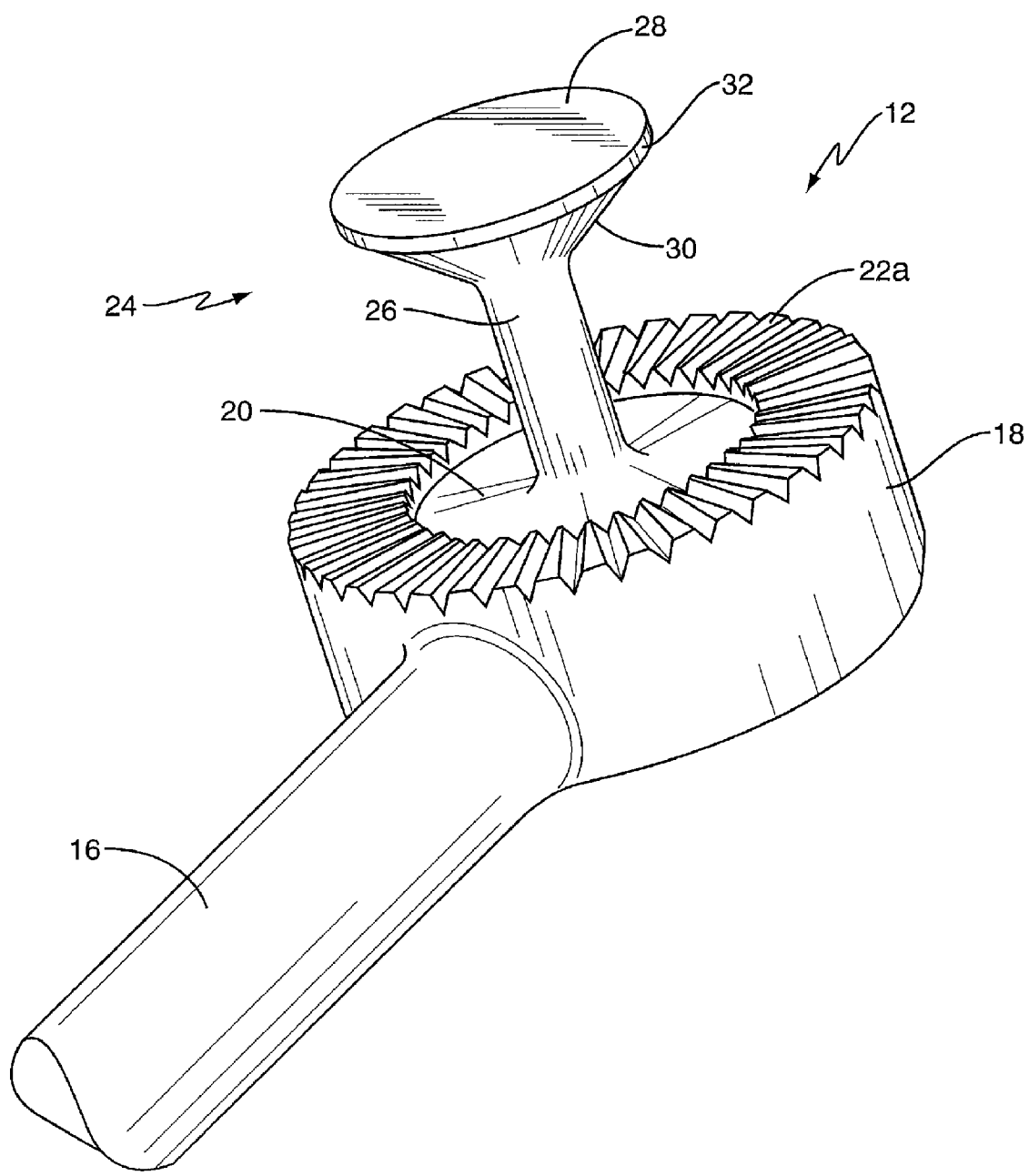
FIG. 2 is a perspective view of a first member of a vertebral rod assembly according to one embodiment.

FIG. 2 illustrates the first member 12 having a rod 16 and a base 18. In one embodiment, the rod 16 is attached to the base 18 and extends outward therefrom. In one embodiment, rod 16 and base 18 are integrally formed together. Base 18 includes a first surface 20 having a plurality of splines 22a spaced thereabout forming a series of alternating ridges and valleys. Splines 22a cover at least a portion of the first surface 20. In one embodiment, the splines 22a are spaced about the periphery, and extend radially inward from an outer edge of the first surface 20 towards a central point as can be seen in FIG. 2. In another embodiment, the splines 22a extend outwards from about the central point of the first surface 20 towards the periphery.

An extension 24 extends outward from the first surface 20 and includes a shaft 26 having an angled surface 30 that flares outward to form an enlarged head 28. Surface 30 slopes outward away from the first surface 20 and terminates at a flat outer surface of the head 28. A rim 32 may be positioned at the peripheral edges of the angled surface 30 and the head 28.

Figure 3:
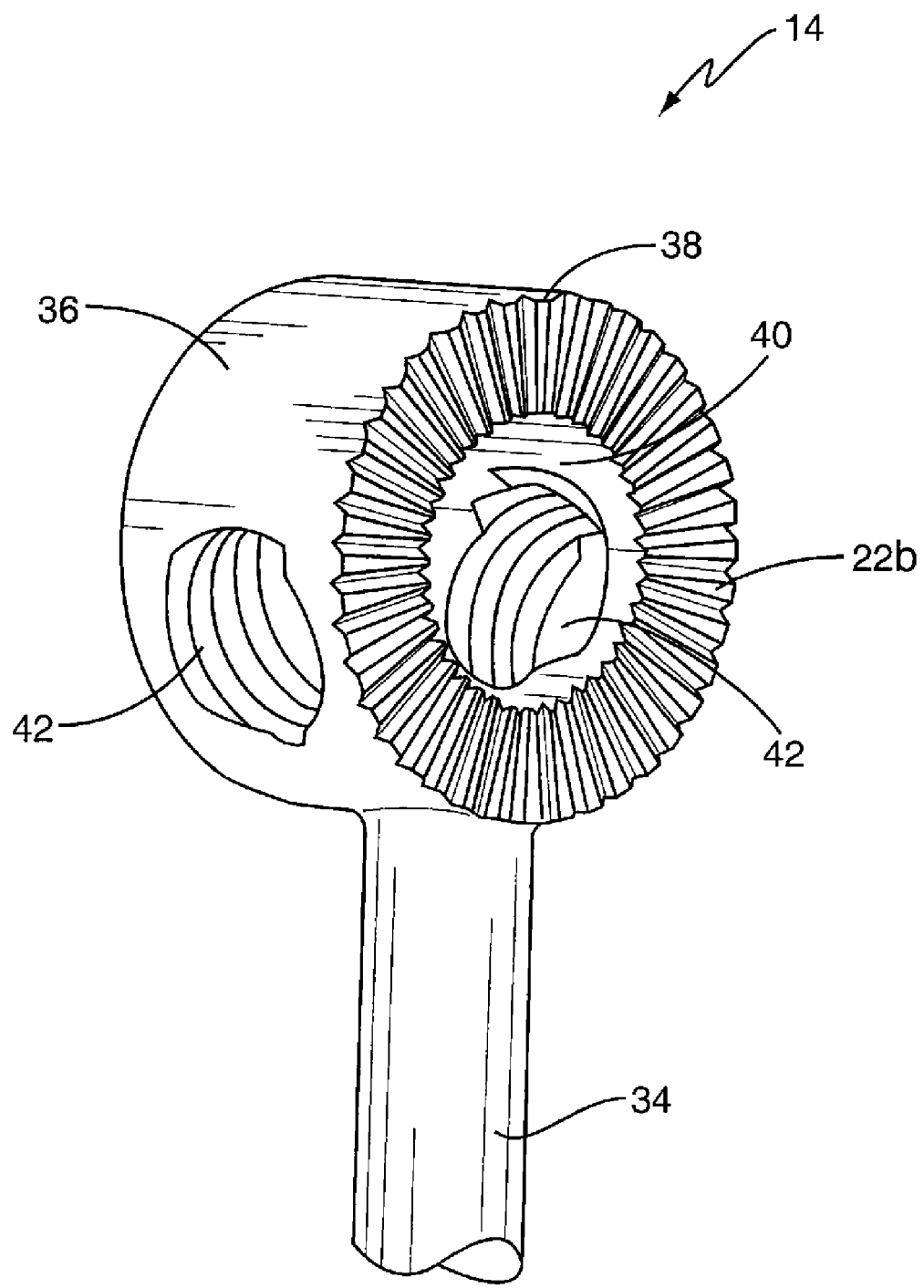
FIG. 3 is a perspective view of a second member of a vertebral rod assembly according to one embodiment.

FIG. 3 illustrates the second member 14 having a rod 34 and a base 36. As with the first member 12, rod 34 is attached to or integrally formed with the base 36 and extends outward therefrom. Base 36 includes a first surface 38 having a plurality of splines 22b formed as alternating ridges and valleys. Splines 22b are formed to correspond to the size and spacing of splines 22a on the first member 12. An opening 40 extends from the first surface 38 into the interior of the base 36 and is sized to receive the extension 24. One or more openings 42 are formed in a sidewall of the base 36 and extend into the interior of the base 36. In one embodiment, a pair of openings 42 are positioned in the base 36 and spaced apart by about 180° (i.e., the openings 42 are on opposite sides of the base 36). Multiple openings 42 allow for easier access during the locking and unlocking procedures as will be discussed below. In one embodiment, the one or more openings 42 may be threaded.

Figure 4:
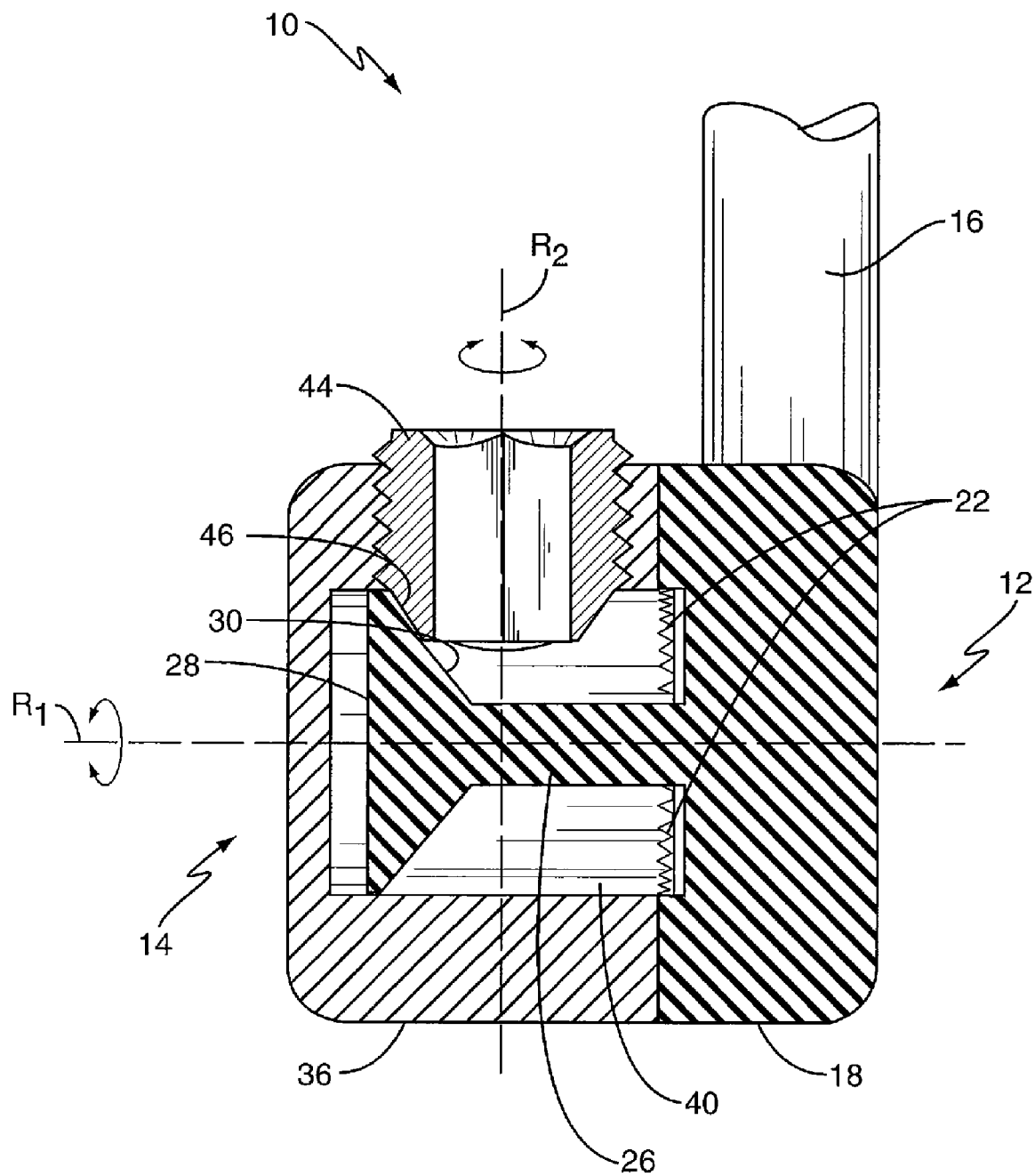
FIG. 4 is a cross sectional view of one embodiment of a vertebral rod assembly.

A fastener 44 extends through the opening 42 formed in the base 36. In the embodiment illustrated in FIG. 4, fastener 44 is a screw having threads that engage the threads formed on the opening 42. Fastener 44 inserts into the opening 42, and has a contact surface 46 that contacts against the surface 30 of the extension 24. The surfaces 30, 46 have corresponding shapes to increase the area of contact between the fastener 44 and extension 24 when the first and second members 12, 14 are coupled in a locked configuration. As illustrated in FIG. 4, the contact surface 46 at the end of the fastener 44 is angled and corresponds to the angle of surface 30. In other embodiments, however, surfaces 30, 46 may not have corresponding shapes. In still other embodiments, fastener contact surface 46 and/or the inserted end of the fastener 44 are shaped to engage the shaft 26.

FIG. 4 illustrates the assembly 10 in a locked configuration. Placing the first and second members 12, 14 in this locked configuration prevents the first and second members 12, 14 from rotating relative to each other about an axis of rotation $R_1$. To rotate the first and second members 12, 14 about axis $R_1$, the assembly 10 may be placed in an unlocked configuration as described below in more detail.

As seen in FIG. 4, the extension 24 of base 18 inserts into the opening 40 formed in the base 36. When extension 24 is fully inserted, splines 22a and 22b engage and interlock with each other. Once engaged, the interlocking splines 22a, 22b prevent the relative rotation of the first and second members 12, 14. Fastener 44 inserts into opening 42 and is rotated about an axis $R_2$ until fastener 44 engages second member 14. In a particular embodiment, fastener 44 inserts into opening 42 and is rotated about axis $R_2$ until the contact surface 46 engages the angled surface 30 of extension 24. Continuing to rotate fastener 44 about axis $R_2$ causes the contact surface 46 to apply a force to the angled surface 30 that locks the second base 36 to the first base 18. This prevents the separation and rotation of the first and second members 12, 14. This force also maintains the splines 22a, 22b in the interlocking relationship. In the embodiment of FIG. 4, the axis of rotation $R_2$ is substantially perpendicular to the axis of rotation $R_1$. In other embodiments, the axis of rotation $R_2$ is substantially non-parallel to the axis of rotation $R_1$.

To place the assembly 10 in the unlocked configuration, in one embodiment fastener 44 is rotated about axis $R_2$ such that contact surface 46 moves away from surface 30. This movement releases the locking force that contact surface 46 applies to the angled surface 30. This movement also allows for disengaging the interlocked splines 22a, 22b. Once the splines 22a, 22b are disengaged, the first and/or second members 12, 14 may be rotated relative to each other by rotating first and/or second bases 16, 34 about axis $R_1$. It is not necessary to separate the contact surface 46 from the angled surface 30 completely, nor is it necessary to remove fastener 44 from base 36 altogether. Rather, it is enough to rotate fastener 44 a sufficient amount to reduce the force applied by the contact surface 46 to the angled surface 30 and to disengage the splines such that the first and second members 12, 14 may rotate relative to one another.

Multiple openings 42 within the sidewall of the base 36 provide additional options for locking the device. Positioning the members 12, 14 along the spine at the proper angle may result in one of the openings 42 being blocked. In this event, the fastener 44 may be inserted into a second opening 42 that is accessible. Additionally, more than one fastener 44 may be used for engagement with a different fastener 44 inserted within each of the openings 42.

Figure 5:
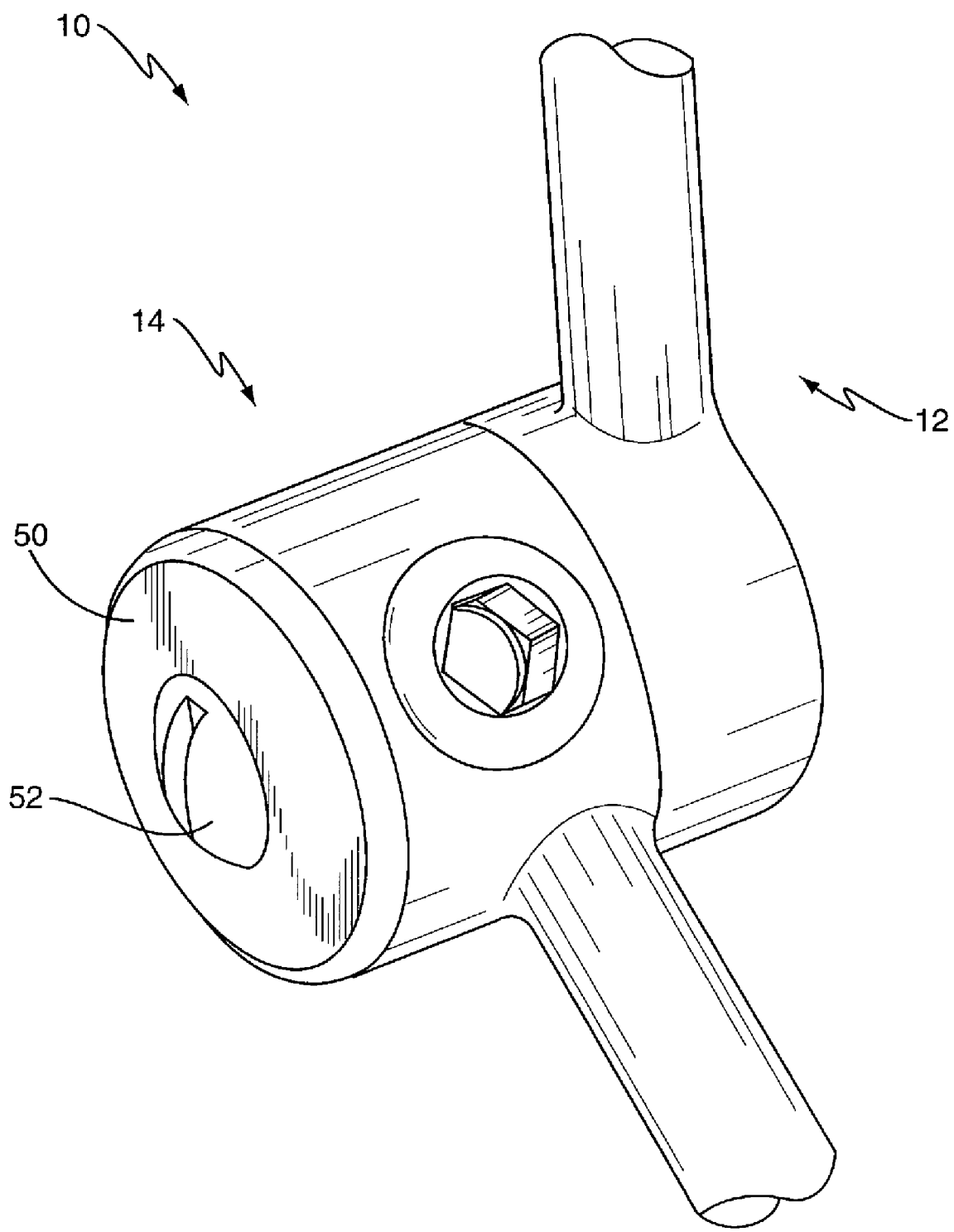
FIG. 5 is a perspective view of a vertebral rod assembly according to one embodiment.

FIGS. 5-10 illustrate another embodiment of assembly 10. As seen in FIG. 5, assembly 10 comprises the first and second members 12, 14, and an end cap 50 coupled to assembly 10 using a mechanical fastener 52. As in the previous embodiment, the first and second members 12, 14 are selectively positionable at a variety of angles to conform the first and second rods 16, 34 generally to the curvature of the patient's spine.

Figure 6:
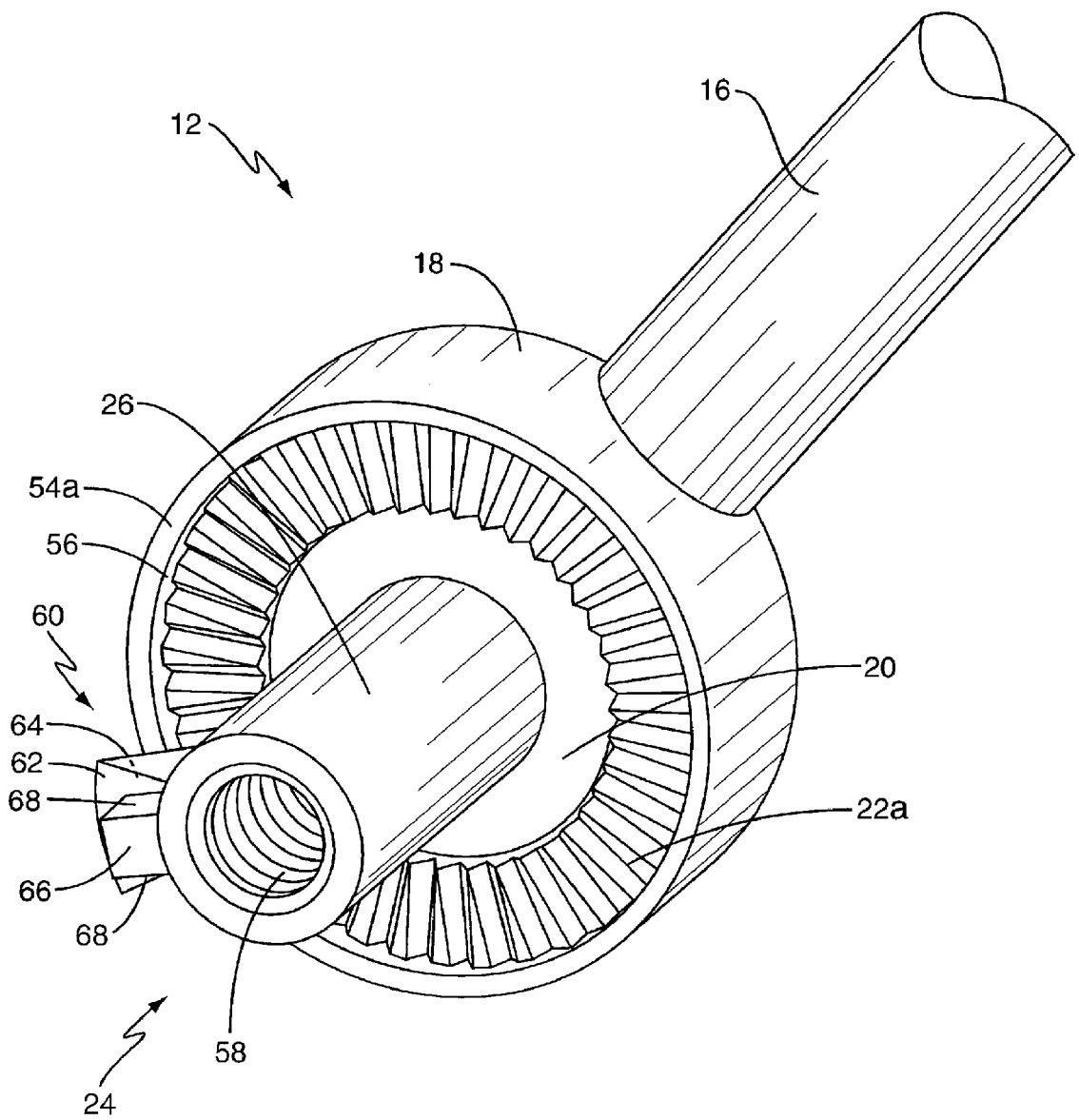
FIG. 6 is a perspective view a first member of a vertebral rod assembly according to one embodiment.
Figure 7:
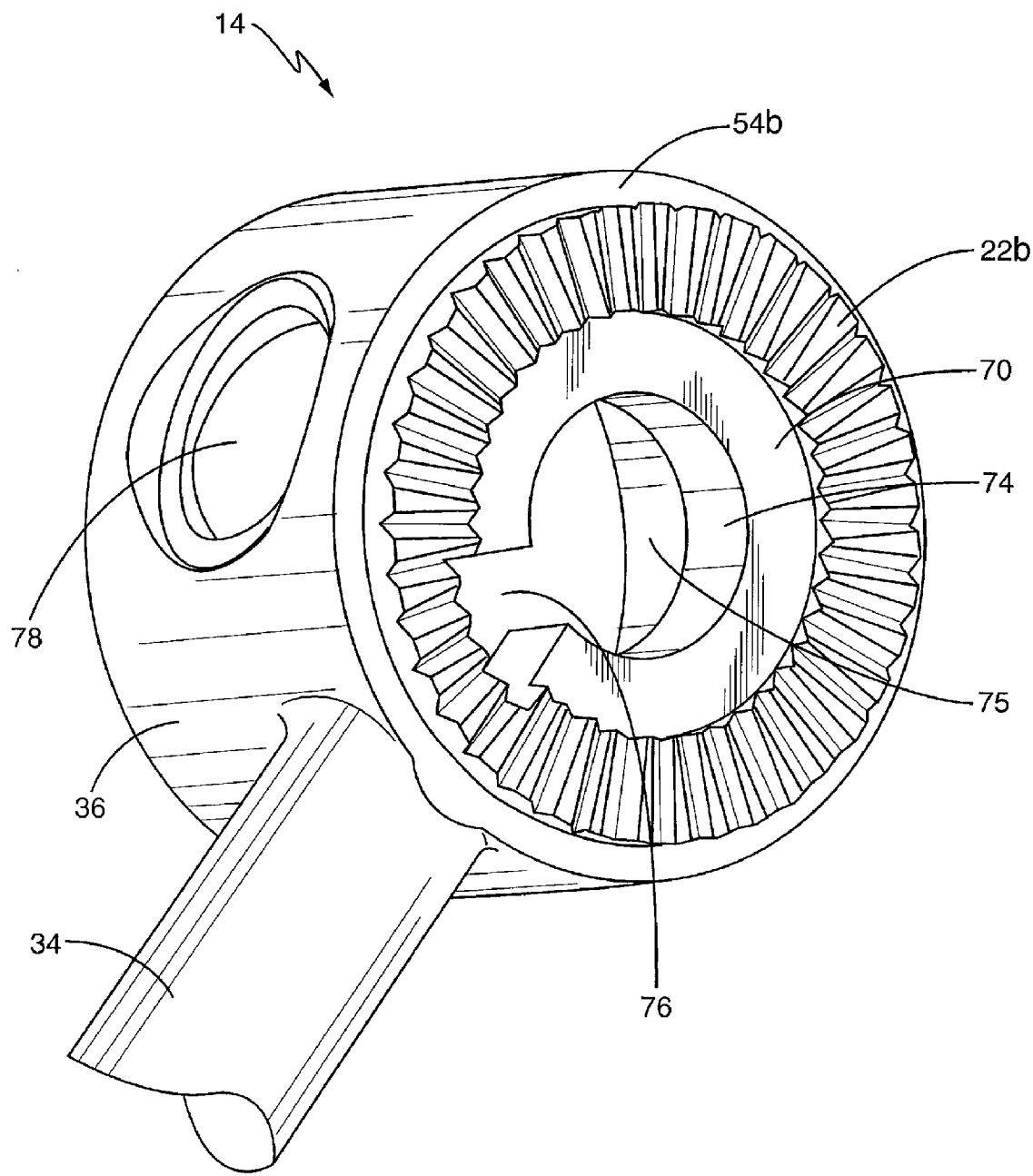
FIG. 7 is a perspective view a second member of a vertebral rod assembly according to one embodiment.

FIGS. 6-7 illustrate the first and second members 12, 14 in more detail. As seen in FIG. 6, surface 20 comprises splines 22a formed as a plurality of alternating ridges and valleys that extend radially inward from a sidewall 56. Splines 22a are spaced inward from the sidewall 56 forming a generally flat edge surface 54a that extends around the periphery of base 18. Shaft 26 comprises a substantially cylindrical member that connects to and extends outward from surface 20. A threaded opening 58 at one end of shaft 26 extends into the shaft 26. The threaded opening 58 is formed to receive the mechanical fastener 52 that secures the end cap 50 to assembly 10.

Shaft 26 also includes a tab 60 extending from its exterior sidewall. Tab 60 includes a ramped surface 64 that terminates at surface 62 that extends substantially perpendicular from the shaft 26. A stop 66 extends outward beyond the surface 62 and has one or more opposing contact surfaces 68. As described below in more detail, tab 60 comprises part of the locking device that locks the position of the first and second members 12, 14 at the desired orientation and may limit the angle through which the first and second members 12, 14 may rotate.

As best seen in FIG. 7, second member 14 includes a surface 70 having splines 22b comprising a plurality of ridges and valleys that extend radially inward towards the center of base 36. The size and spacing of splines 22b corresponds generally to splines 22a. A generally flat edge surface 54b extends between splines 22b and the peripheral edge of base 36. When the first member 12 is mated to the second member 14, the splines 22b extend into the base 18 to engage with the splines 22a. Additionally, the flat edge surface 54b contacts corresponding flat edge surface 54a on base 18.

An opening 74 with a notch 76 are formed in the surface 70, and open into a receiving section 75. Opening 74 and notch 76 are sized to receive the shaft 26 and the tab 60, respectively, when the first member 12 mates with the second member 14. One or more openings 78 are formed in a sidewall of the base 36 and extend into the receiving section 75. The openings 78 may be disposed at any desired position on the sidewall of base 36. Centerlines of the openings 78 may be perpendicular to centerlines of the opening 74. As described in more detail below, the fastener 44 extends through the opening 78 to lock the first and second members 12, 14.

Figure 8:
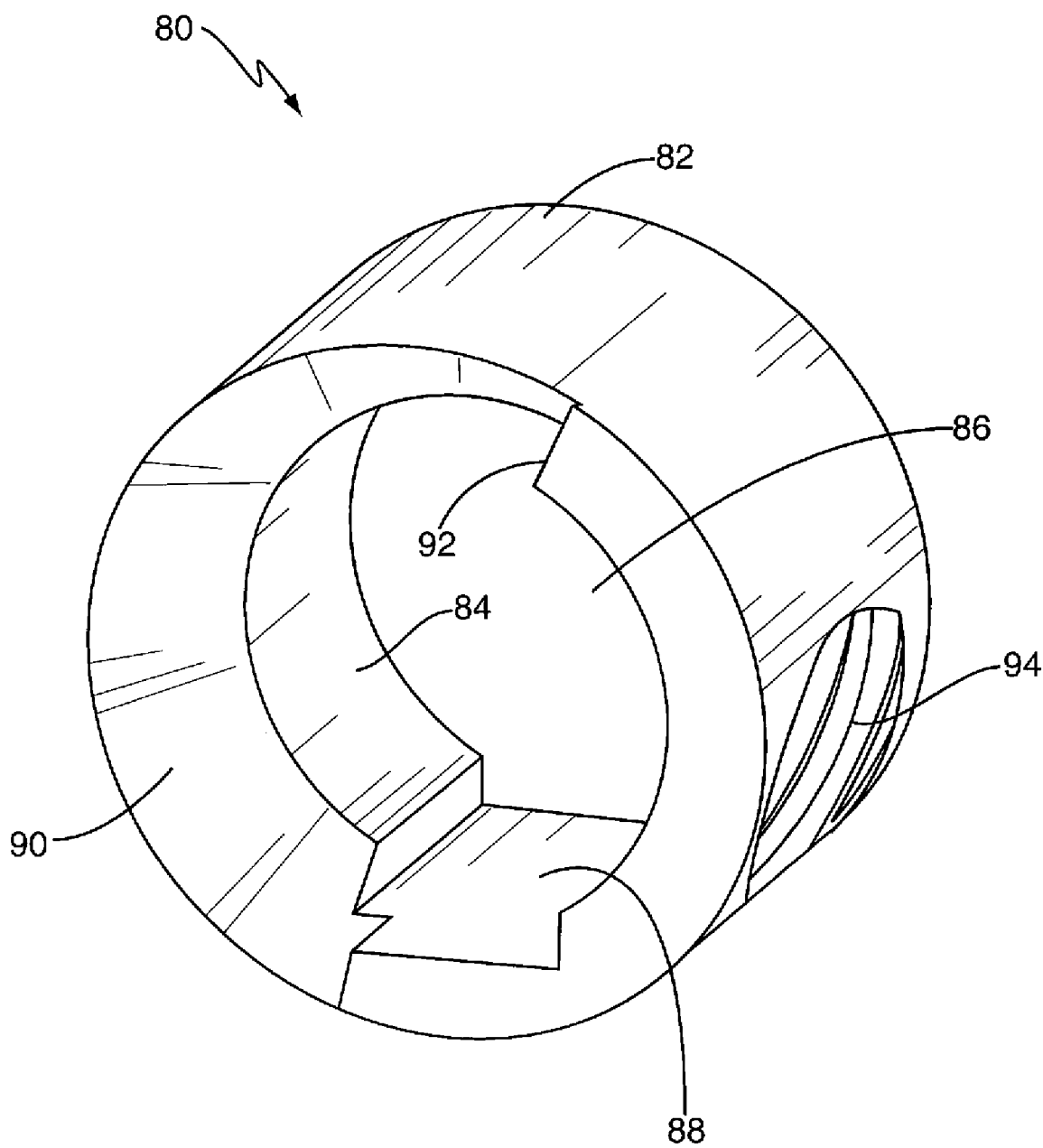
FIG. 8 is a perspective view of a ring member according to one embodiment.

FIG. 8 illustrates a ring 80 that fits within the receiving section 75 and extends around the shaft 26. Ring 80 is a substantially cylindrical member that includes an outer sidewall 82 and an inner sidewall 84 that form a cavity 86. A notch 88 is formed on the inner sidewall 84 to receive the tab 60 extending from the shaft 26. An angled surface 90 slopes upward from a peripheral edge of the inner sidewall 84 and is angled to correspond to the angle of the ramped surface 64. Angled surface 90 also extends around the inner circumference of the ring 80 from the notch 88 to a stop surface 92. A threaded opening 94 extends through the ring into the cavity 86 and is sized to receive fastener 44.

In one embodiment, a stop surface 92 is formed at one end of the angled surface 90. Stop surface 92 contacts the stop 66 on the tab 60 to control the extent of relative rotation of the first and second members 12, 14. During rotation, the ramped surface 64 may slide along angled surface 90 until the contact surface 68 of the stop 66 engages the stop surface 92. In one embodiment as illustrated in FIG. 8, members 12, 14 rotate through an angle of approximately 180°. However, those skilled in the art will readily appreciate that the stop surface 92 may be formed on the ring 80 at any position such that the first and second members 12, 14 may only rotate a predetermined distance in one direction to limit the rotation.

Figure 9:
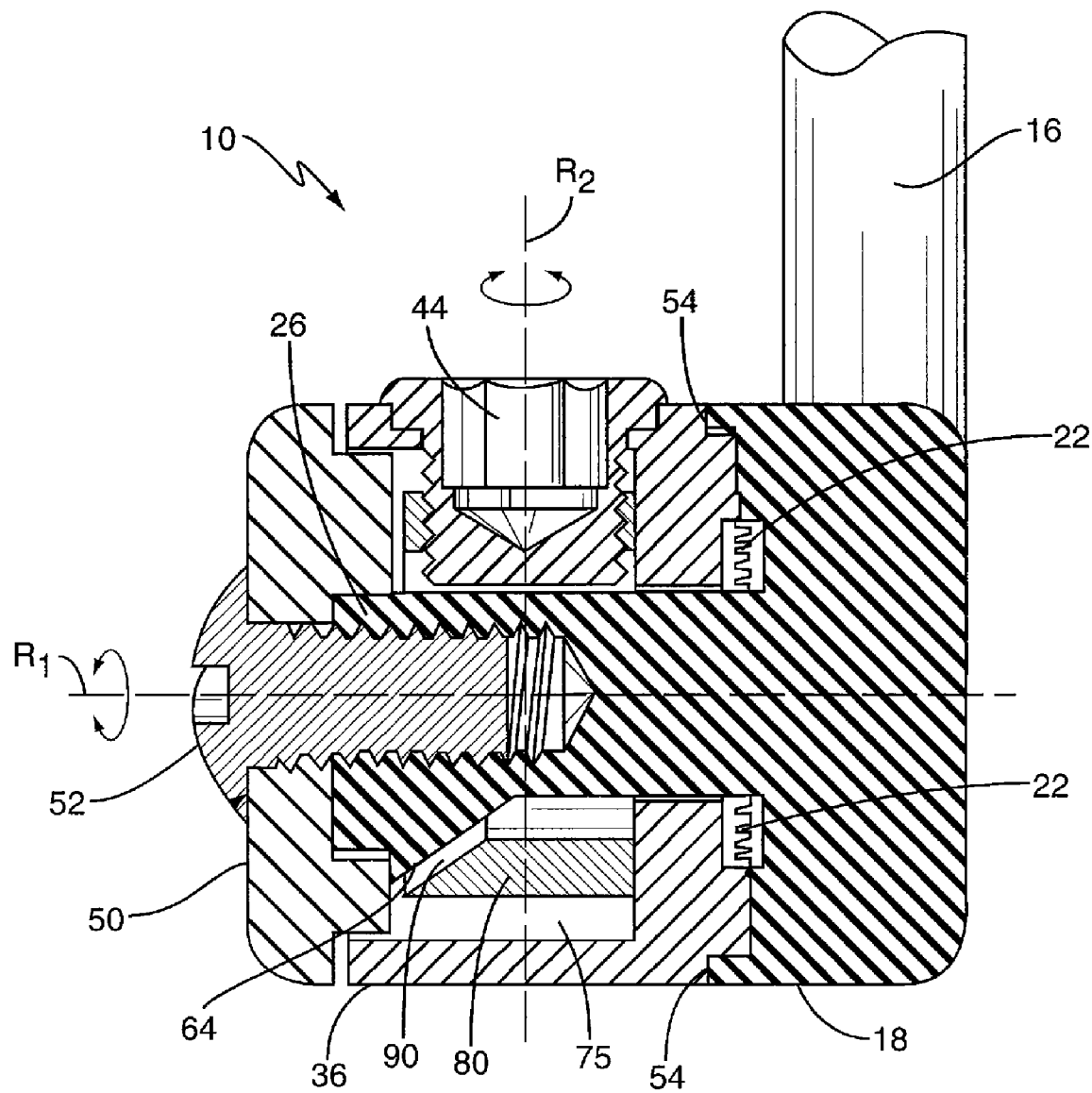
FIG. 9 is a cross sectional view of one embodiment of a vertebral rod assembly.

FIG. 9 illustrates a cross sectional view of the assembly 10. As in the previous embodiment, placing the first and second members 12, 14 in this locked configuration prevents the first and second members 12, 14 from rotating relative to each other about the axis of rotation $R_1$. During assembly, ring 80 is positioned within the receiving section 75 with opening 94 in the ring aligning with the opening 78 in the base 36. An outer diameter of the ring 80 is smaller than an inner diameter of the receiving section 75 such that the ring 80 can move along axis $R_1$ within the receiving section 75. Further, the shaft 26 inserts into the opening 74 with the tab 60 aligning with the notch 76 in the opening and the notch 88 in the ring 80. Fastener 44 is initially inserted into openings 78, 94.

Prior to tightening the fastener 44, first and second members 12, 14 are rotated to position the rods 16, 34. Once oriented, fastener 44 is tightened causing the ring 80 to move along axis $R_2$ within the receiving section 75 towards the fastener 44. This movement, in turn, causes the angled surface 90 on the ring 80 to contact and apply a locking force to the ramped surface 64 on the tab 60. Adjusting the fastener 44 within the openings 78, 94 adjusts the degree of the locking force and thus prevents further rotation of the first and second members 12, 14.

When the first and second members 12, 14 are positioned together, the splines 22b formed on base 36 engage and interlock with the splines 22a formed on base 16. This engagement further prevents rotation of the first and second members 12, 14. In addition, flat edge surfaces 54a and 54b contact each other to form a substantially smooth seam extending around the circumference of the first and second bases 18, 36.

End cap 50 may be connected to assembly 10 using screw 52. End cap 50 is sized to extend across the receiving section 75. End cap 50 may further include a gasket to sealingly engage the sidewall of the base 36 and seal the receiving section 75.

Figure 10:
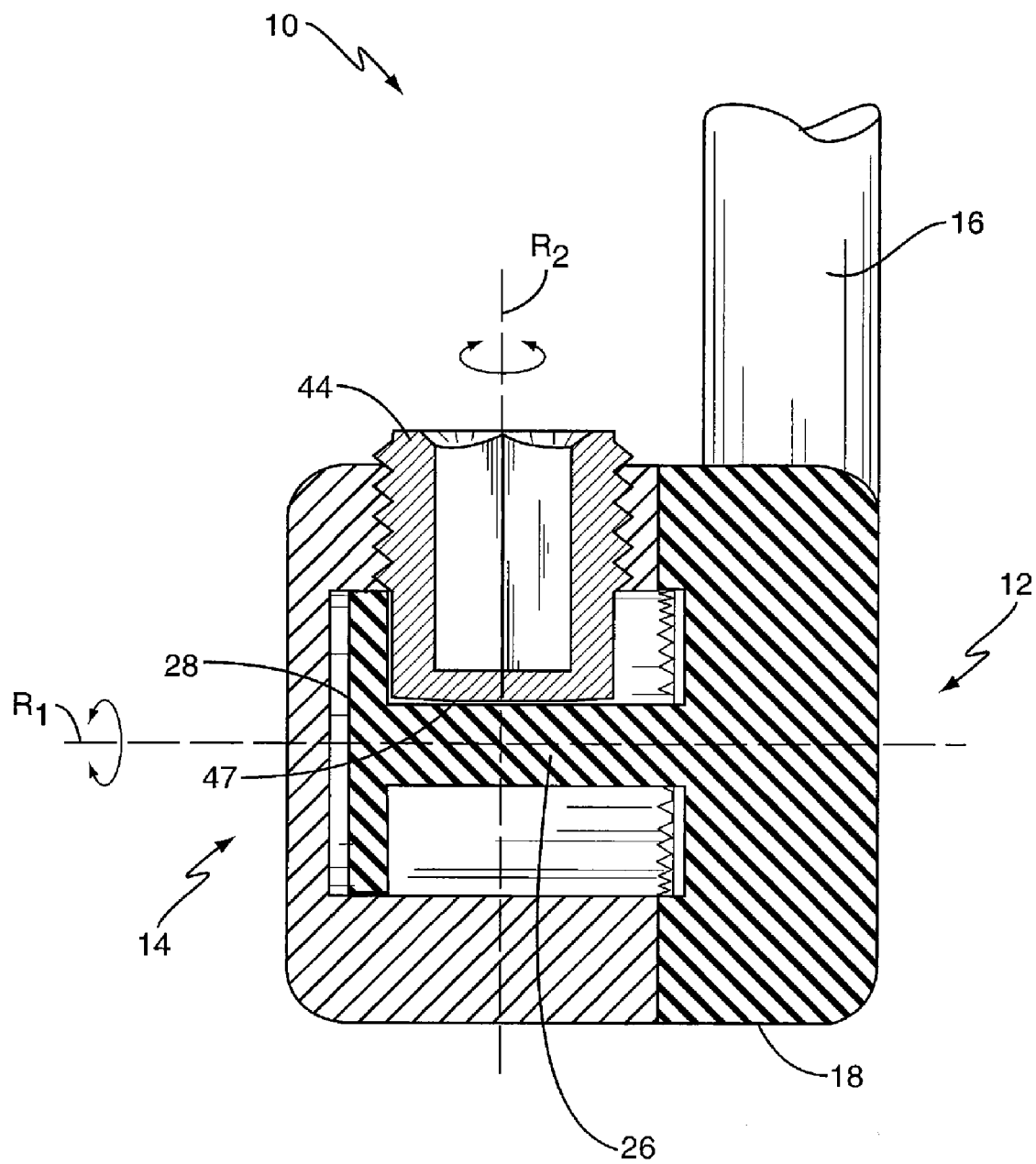
FIG. 10 is a cross sectional view of one embodiment of a vertebral rod assembly.

FIG. 10 illustrates another embodiment with a shaft 26 that terminates at a head 28. Both the shaft 26 and head 28 have a substantially constant width that form a "T". Fastener 44 includes a contact surface 47 that engages the shaft 26 to lock the device 10. Contact surface 47 substantially matches the shaft 26 to increase the contact area. Fastener 44 may further be positioned for an edge to contact the head 28 to further lock the device 10. In one embodiment, the locking force is provided between the contact surface 47 and the shaft 26. In another embodiment, the locking force is provided between the edge of the fastener 44 and head 28.

The various figures have illustrated bases 18 and 36 as having a circular shape. However, bases 18 and/or 36 may have other shapes and sizes. Further, the shapes and sizes of the bases 18, 36 may be the same or may be different. Likewise, the various openings may have different shapes and sizes to receive one or more various sizes and/or types of fasteners.

Rods 16 and 34 may have variety of lengths and diameters. The lengths and/or diameters of one or both of the rods 16, 34 may be the same or different. Moreover, one or both of the rods 16, 34 may be integrally formed with the sidewalls of their respective bases 16, 36, or formed separately and attached to the sidewalls of their respective bases 18, 36. Further, splines 22a, 22b may extend continuously around their respective bases 16, 34 or alternatively, may be formed in sections that are spaced apart along the surfaces of the first and second bases 18, 36.

In one embodiment, axes of rotation R1 and R2 are substantially perpendicular. Examples include the embodiment illustrated in FIGS. 4, 9, and 10. In other embodiments, however, the axes are aligned at a variety of angular orientations. Further, axis R2 may be aligned to be substantially parallel with one or both rods 16, 34. In other embodiments, axis R2 may be positioned in a non-parallel manner.

The present invention may be carried out in other ways than those specifically set forth herein without departing from essential characteristics of the invention. A seal may be placed on one or both bases 18, 36 to sealingly engage the bases together in the locked configuration. The present embodiments are to be considered in all respects as illustrative and not restrictive, and all changes coming within the meaning and equivalency range of the appended claims are intended to be embraced therein.

What is claimed is:

1. A vertebral rod assembly comprising:
a first member having a first base and a first vertebral rod extending in a first direction from the first base;
an extension extending outward from the first base in a second direction;
a second member having a second base and a second vertebral rod extending from the second base;
a receiving section formed within the second base and including a first opening sized to receive the extension that extends from the first base, the receiving section further including a second opening through a sidewall of the receiving section, each of the first and second openings extending into the receiving section and being spaced apart from one another;
a ring sized to be disposed within the receiving section, the ring including an exterior wall that forms a central cavity sized to receive the extension, the ring also including a third opening that extends through the exterior wall and leads into the central cavity; and
a fastener extending through the second opening in the receiving section and the third opening in the ring to lock the second base to the first base to prevent relative movement between the first and second vertebral rods.

2. The assembly of claim 1 further comprising an end cap with a fourth opening, the end cap sized and configured with the fourth opening aligned with an axial end of the extension and extend across and cover the receiving section.

3. The assembly of claim 1 wherein the extension comprises a tab having a first contact surface that extends radially outward from the extension, and wherein the ring comprises a second contact surface that engages the first contact surface to lock the first and second bases.

4. The assembly of claim 3 wherein the first and second contact surfaces have substantially complementary angles to slidingly engage each other when the first member rotates relative to the second member.

5. The assembly of claim 1 wherein centerlines of the first and second openings of the receiving section are perpendicular.

6. The assembly of claim 1 wherein the fastener is spaced away from the extension when the second base is locked to the first base.

7. The assembly of claim 1 wherein each of the first and second members includes splines that engage together when the second base is locked to the first base.

8. A vertebral rod assembly comprising:
a first member having a first base and a first vertebral rod;
an extension extending outward from a first surface of the first base;
a second member having a second base and a second vertebral rod, the second base having a receiving section formed by a sidewall and a lower base wall, the receiving section being sized to receive the extension;
a ring disposed within the receiving section and including a central cavity sized to extend around the extension, the ring also including a second opening, the ring being positioned between the extension and the sidewall; and
a fastener extending into a first opening in the second base and the second opening in the ring at points spaced from the first and second vertebral rods, the fastener applying a force to the ring to lock the second base to the first base.

9. The assembly of claim 8 wherein the ring comprises a contact surface along an inner peripheral edge that contacts the extension to lock the ring to the first member.

10. The assembly of claim 8 wherein the first surface of the first base includes a first set of splines and an outer surface of the lower base wall that faces away from the receiving section includes a second set of splines, the first and second sets of splines engaging together to lock the second base to the first base.

11. A vertebral rod assembly comprising:
a first base positioned at an end of a first vertebral rod, the first base including an outwardly-extending shaft that extends outward from a first surface of the first base and is perpendicular to the first vertebral rod, the first base further including a ramp that extends radially outward from the shaft at a point spaced away from the first surface;
a second base positioned at an end of a second vertebral rod, the second base including a lower wall and outwardly-extending sidewall that form a receiving section, the second base including an opening in the lower wall that extends into the receiving section and is configured to receive the extension, the second base further including a first threaded opening in the sidewall;
a ring formed by a wall and including a second threaded opening in the wall and an angled contact surface at an axial end of the wall, the ring sized to fit within the receiving section and extend around the extension with the second threaded opening being aligned with the first threaded opening; and
a threaded fastener sized to fit into the first and second threaded openings and apply a force to the ring to move the angled contact surface into contact with the ramp and lock the second base to the first base.

12. The assembly of claim 11 wherein the first base further includes a first set of splines on the first surface and the second base includes a second set of splines on the lower wall, the first and second sets of splines configured to engage together to lock the second base to the first base.

13. The assembly of claim 11 wherein the opening in the lower wall of the second base includes a notch that extends radially outward from the opening and is sized to receive the ramp of the first base.

14. The assembly of claim 11 wherein centerlines of the opening and the first threaded opening are perpendicular.

15. The assembly of claim 11 wherein the threaded fastener is spaced away from the extension when the second base is locked to the first base.

16. The assembly of claim 11 wherein each of the first base and the second base include circular shapes with an axial end of the sidewall contacting against a circular edge of the first base during positioning of the vertebral rods.

17. The assembly of claim 11 wherein the ring includes a notch along an inner surface of the wall.

18. The assembly of claim 11 wherein the fastener is parallel to each of the first and second vertebral rods when positioned in the first and second threaded openings.

19. The assembly of claim 11 wherein the lower wall of the second base is positioned between the ring and the first surface of the first base when the second base is locked to the first base.

20. The assembly of claim 11 further comprising an end cap sized to extend across the receiving section and a fastener that extends through an opening in the end cap and into the extension to maintain the position of the end cap.

* * * * *